United States Patent [19]

Nielsen

[11] Patent Number: 5,334,932

[45] Date of Patent: Aug. 2, 1994

[54] TEMPERATURE COMPENSATED ELECTRICAL SENSOR SYSTEM FOR MEASURING FERROUS PARTICLES IN A FLUID USING A SERIES RESONANT OSCILLATOR AND MICROPROCESSOR

[75] Inventor: Paul H. Nielsen, Wilmington, Del.

[73] Assignee: Vickers Incorporated, Glenolden, Pa.

[21] Appl. No.: 813,353

[22] Filed: Dec. 24, 1991

Related U.S. Application Data

[63] Continuation of Ser. No. 659,110, Feb. 22, 1991, abandoned.

[51] Int. Cl.$^5$ .................. G01N 27/74; G01R 33/12
[52] U.S. Cl. .................. 324/204; 324/225; 324/236
[58] Field of Search .................. 324/204, 237, 225

[56] References Cited

U.S. PATENT DOCUMENTS

| | | |
|---|---|---|
| 4,004,216 | 1/1977 | Natens et al. |
| 4,731,578 | 3/1988 | Tsaprazis .................. 324/204 |
| 4,831,362 | 5/1989 | Tsaprazis .................. 324/204 X |
| 4,859,940 | 8/1989 | Hummert et al. .................. 324/237 X |
| 4,878,019 | 10/1989 | Tsaprazis et al. .................. 324/204 |

FOREIGN PATENT DOCUMENTS

| | | |
|---|---|---|
| 0049304 | 4/1982 | European Pat. Off. |
| 0284711 | 10/1988 | European Pat. Off. |
| 56-8562 | 1/1981 | Japan. |
| 56-8563 | 1/1981 | Japan. |
| 56-8567 | 1/1981 | Japan. |
| 2207765 | 2/1989 | United Kingdom. |
| 2219405 | 12/1989 | United Kingdom. |

*Primary Examiner*—Gerard R. Strecker
*Assistant Examiner*—Warren S. Edmonds
*Attorney, Agent, or Firm*—Robert S. Lipton

[57] ABSTRACT

A magnetic sensor for the collection and measurement of ferrous particles through the use of an electronic tuned circuit is disclosed. The sensor contains an electrical inductance coil along with an integral magnet to attract ferrous particles suspended in the fluid. The ferrous particles collecting on the magnetic surface of the sensor causes a change in the inductance of the integral coil which is measured by an electronic circuit. The electronic circuit operating in conjunction with the sensor utilizes a series resonant circuit. A measurement of the voltage across the series resonant circuit is responsive to changes in temperature of the inductance coil. A microprocessor is used to determine the change in period of the resonant oscillation with change in inductance of the coil. The microprocessor uses the data on temperature variation to correct the observed change in oscillator period for the effects of temperature. The sensor may be located in environmental conditions which include a large variation in ambient temperature. The microprocessor may be interrogated to obtain information on the total debris accumulated, the presence of any rapid or large debris accumulation and the variation of the temperature in the probe.

2 Claims, 5 Drawing Sheets

TEMPERATURE COMPENSATED ELECTRICAL SENSOR SYSTEM FOR MEASURING FERROUS PARTICLES IN A FLUID USING A SERIES RESONANT OSCILLATOR AND MICROPROCESSOR

This application is a continuation of patent application Ser. No. 07/659,110 filed Feb. 22, 1991, entitled "An Electrical Sensor System For Measuring Ferrous Particles Within A Fluid Utilizing A Series Resonant Oscillator and Microprocessor" by Paul H. Nielsen, now abandoned.

BACKGROUND OF THE INVENTION

The disclosed invention relates to means for detecting and measuring ferrous particles in a fluid medium, and it is of particular use for detecting ferrous particles in the lubricant of an engine or mechanical transmission. In such an application, the monitoring of such particles may be utilized to give warning of malfunction or other mechanical breakdown of the engine or transmission. The invention disclosed is of particular importance for the operation of an internal combustion engine, especially highly stressed helicopter and aircraft engines wherein prior warning of a malfunction permits corrective action prior to catastrophic failure.

Metal parts in the internal combustion or mechanical transmission, e.g., gear boxes, undergo wear because of friction between the metallic parts or a metal part and a non-metal part. The result of the wearing friction is metallic contamination of the lubricant or transmission fluid. The contamination comprises metal particles of many sizes and shapes. Monitoring of the metal particles contained in the fluid can provide early warning of the deterioration of a mechanical device such as the internal combustion engine or its associated operating systems such as mechanical power transmissions or other gear boxes.

SUMMARY OF THE INVENTION

The present invention uses magnetic attraction to capture ferrous particles circulating in the fluid system. An electrical inductance coil situated around a permanent magnet is used as a probe for insertion into an oil gear box for the metering of metallic debris therein. As ferrous particles are captured on the permanent magnet containing the sensor probe, the electrical inductance of the probe is thereby changed due to the proximity of the various particles through the coil. The inductance coil is part of a series resonant circuit. The change in inductance of the inductance coil is used to change the frequency of an oscillator based on the series resonant circuit. The change in the period of oscillation is monitored, and processed electronically by a microprocessor to relate to the amount of debris accumulation upon the sensor probe.

An inherent problem in the monitoring for ferrous particles in a lubricant such as an aircraft power transmission is the problem of widely ranging temperature variation. The temperature of a transmission lubricant in an aircraft, or any other engine, can change many hundreds of degrees over its time of operation. Such environmental temperature changes have the propensity to change the operating parameters of an electrical inductance coil, such as the probe used in the present invention. For a typical coil, both the resistance of the wire from which the coil is formed and the inductance of the coil change with temperature. It is possible using a series resonant circuit to obtain a signal dependant on the changing resistance of the inductor which therefor reflects the changing operating temperature of the coil. This signal may be used to provide temperature compensation to correct the measured period of the oscillator thereby improving the accuracy of the inductance measurement.

It is the principal object of the present invention to provide a ferrous particle capture device for use in a circulating liquid system wherein the mass of the total accumulated particles so captured are measured. It is a further object of the present invention to provide signals which are a function of the mass accumulated on the particle capturing device for the estimation of the amount of material accumulated. It is a further object of the invention to provide an indication of larger debris particles or rapid accumulation of debris particles. It is also the object of the present invention to provide a temperature compensating means to increase the accuracy of the signal generated which represents the mass of the total accumulated particles captured over a wide increase or decrease in ambient temperature of the probe.

DETAILED DESCRIPTION OF THE INVENTION

The present invention utilizes debris collection means such as that disclosed in U.S. Pat. No. 4,731,578 issued on Mar. 15, 1988 entitled "An Electrical Sensing System for Measuring Ferrous Particles Within a Fluid". The present invention is a method of collecting and measuring the quantity of ferrous particles suspended in a fluid such as lubricating oil in a transmission. It is desirable to monitor the amount of ferrous particles or debris which may be suspended in a lubricating fluid such as transmission oil in a gear box or internal combustion engine. To collect such ferrous material at a location to perform such monitoring, it is desirable to place a permanent magnet within the fluid to attract such particles. Once such ferrous particles begin to collect on a magnetic surface, they can be further measured so that it may be determined what total amount of ferrous particles may be suspended in such fluid. The presence of such ferrous particles frequently indicates impending mechanical failure.

Upon collection of the ferrous particles upon a magnet, it is possible to measure the quantity of such particles by introducing an electrical inductor in the vicinity of such ferrous particles. It is well known that changing the core material in the proximity of an electrical inductor will cause a change in the inductance value of that inductor. Therefore, measuring the inductance change of an electrical coil in the vicinity of a collection of ferrous particles upon a magnet can provide an input means to ultimately measure the amount of such particles being collected.

Figure 1:
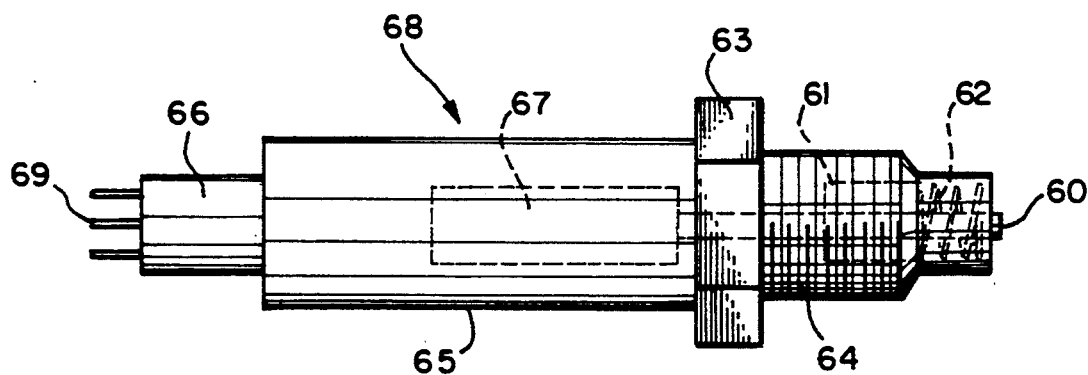
FIG. 1 is a view of the type of sensor probe to be used for insertion within a reservoir of fluid containing ferrous particles to be measured.

Turning to FIG. 1 of the drawings, an electrical sensor plug 68 for collecting ferrous particles within the fluid as shown. A sensor 68 is essentially designed as a plug, such as a drain plug one may find on any fluid carrying vessel, particularly oil sumps and transmission gear oil boxes as found in many different transmission and internal combustion engine systems. Sensor 68 is comprised of the sensor body 65, with an integral wrench nut 63 for fastening the sensor into a frame. Such fastening is facilitated by the surface thread 64 which are threaded to allow the sensor to be bolted into the wall of the container of the fluid to be observed. Magnet 67 is contained within the body of sensor 68. Magnet 67 is a permanent magnet, but does not actually extend through the threaded portion of sensor 68 to the collection surface 60. Magnetic flux is transmitted to collection surface 60 through pole piece 61. Pole piece 61 serves to extend magnetic flux from magnet 67 to collection surface 60 without actually requiring the magnet 67 to be located at the end of sensor 68 which actually protrudes into the fluid to be measured.

Coil 62 is formed within the housing 68 at a location set forth in FIG. 1. This inductor 62 is coaxial with pole piece 61 and is formed so that collection of ferrous material on collection surface 60 serves to alter the inductance of coil 62 by the change in the permeability of the core of 62. It will be appreciated by those skilled in the art that a collection of ferrous material in a location close to an electrical inductor will increase the value of that inductor. In the sensor configuration shown in FIG. 1, the lines of flux produces by magnet 67, transmitted through pole piece 61 to collection surface 60 created an attractive magnetic zone in the vicinity of the collection surface 60. When a ferrous particle enters the magnetic zone and is captured on the collection service 60 it will appreciated that such would change the inductance value of coil 61. coil 61 is connected through two leads, not shown, through the housing 65 to electrical connector 66. Electrical connector 66 is a conventional electrical plug with prong 69 protruding therefrom. Two leads of prong 69 represent the leads from both sides of the coil. The third lead of prong 69 is a grounding prong which is attached ultimately to housing 65. This grounding prong allows a shielded cable to connect coil 62 with any external electronic circuitry as will be described below.

The present invention includes a method of determining, and correcting for, error and drift in the resonant circuit which may be caused by temperature changes. The circuit, in its operation which will be described below, may be utilized in conjunction with sensor 68 to provide an accurate reading of the accumulation of ferrous debris on surface 60. In its more general application, the circuit may be used to measure changes in inductance of an inductor where the inductor is subject to changes in temperature.

In the prior art, parallel resonant circuits have been used extensively in devices designed to measure changes in inductance, and in particular, in devices designed to relate changes in inductance to debris particles accumulating on an electrical inductor probe. An example of such prior art is found in Tsaprazis, et al. U.S. Pat. No. 4,878,019. As shown in Tsaprazis, other approaches have been taken to affecting temperature compensation of these devices when utilizing a parallel resonant circuit. A problem associated with using parallel resonant circuits is that a measure of the current going through such a circuit or of the voltage developed across such a circuit at resonance remains a complex function of the frequency and capacitance and inductance. Thus a measure of the current through the parallel resonant circuit or the voltage developed across it cannot be used in a non-complex manner to provide a temperature compensating correction.

Figure 2:
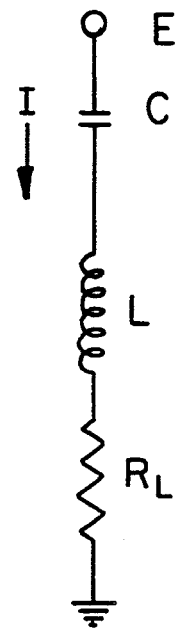
FIG. 2 shows a typical schematic diagram of a series resonant circuit.

However, it has not heretofore been recognized that a series resonant circuit does not suffer from the same deficiency. The voltage developed across a series resonant circuit such as shown in FIG. 2 is equal to: $E = I \times Z$ where the impedance $Z = 1/j\omega C + j\omega L + R_L$. In this equation, $1/j\omega C$ is the impedance of the capacitor, $j\omega L$ is the impedance of the inductor, and $R_L$ is any resistance associated with the wire in the inductor as well as any external resistance in the connection wires. Dividing the voltage by the current yields the effective resistance $E/I = Z = 1/j\omega C + j\omega L + R_L$. The resonant condition for a series resonant circuit occurs when $\omega = 1/\sqrt{LC}$. Multiplying both sides of the equation by one $[j\omega C/j\omega C]$ yields the impedance $Z = 1/j\omega C + [j^2 \omega^2 CL + j\omega CR_L]/j\omega C$ which simplifies to $Z = [1 - \omega^2 CL + j\omega CR_L]/j\omega C$. At the resonant condition of $\omega = 1\sqrt{LC}$, $\omega^2 = 1/LC$, or, $1 = \omega^2 LC$. Substituting for $\omega^2 LC$ in the above equation, yields $Z = [1 - 1 + j\omega CR_L]/j\omega C$, which when simplified, yields $Z = R_L$.

Thus it can be seen that the impedance at resonance of a series resonant circuit is proportional to $R_L$. Therefore, the voltage developed across such a circuit is directly proportional to $R_L$. Clearly, the impedance or the voltage does not depend in a complex way upon the frequency or the capacitance or the inductance as it does in a parallel resonant circuit. As $R_L$ changes with temperature, it is a consequence of the above that the voltage across a series resonant circuit will also now change with temperature and may be used to correct the output of the oscillator for the effects of temperature.

Figure 3:
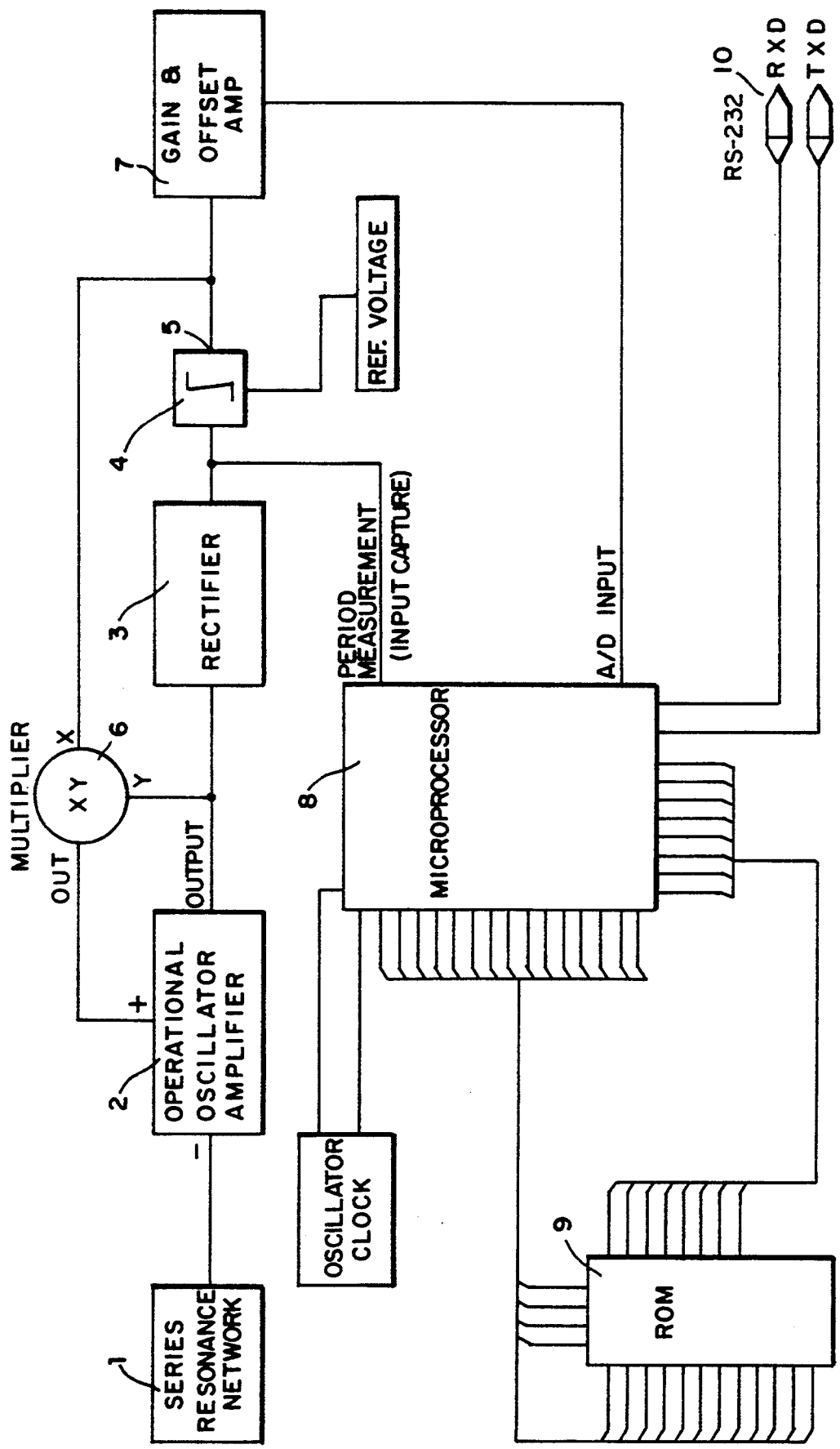
FIG. 3 is an electronic block diagram illustrating the major components of the invention, and is a simplified illustration of the schematic diagram found in FIG. 4.

FIG. 3 shows a schematic block diagram of the system of this invention. The system consists of a inductive sensor in series with a capacitor in a series resonance network, a series resonant self-oscillating detector, and a digital signal processor. The self-oscillating detector operation is based on a series resonance tank design, using an active peak detector and integrator to rectify, and average the sine-wave produced by the oscillator. This rectified average signal is then sent to a precision multiplier in order to multiply it with the original sine-wave to close the system loop, and in turn generate the positive feedback needed to sustain the self-oscillation with minimal peak to peak amplitude variations. The self-oscillation frequency is produced by the values of the series LC network. As the electrical inductor forming part of the sensor accumulates debris, the value of the inductance of the sensor coil will change, thereby changing the resonant oscillating frequency of the detector. The circuit maintains the amplitude of the detector constant. This provides a first order temperature correction or compensation to the circuit.

The output of the oscillator is fed to a microprocessor which measures the change in period of the oscillator as debris accumulates on the probe. The difference in the period from the initial period (measured with no debris particles) is a measure of the amount of debris particles accumulated. Simultaneously, a signal which is proportional to the resistance (temperature) of the sensor coil, is also provided to the microprocessor. The microprocessor calculates a correction factor and applies it to the observed change in period to correct for the temperature difference. The microprocessor may be interrogated through a standard RS-232 serial interface to transmit information with respect to the current change in the period of oscillation as well as the temperature correction to be applied. Alternatively, the microprocessor will output a value of the period which has been corrected for change in temperature, and therefore, a corrected indication of the total amount of debris particles which have accumulated.

As can be seen in FIG. 3, the series resonance network 1 is connected to the negative input of operational amplifier 2. The output of amplifier 2 is rectified by rectifier 3 and applied to integrating comparator 4. The output 5 of integrating comparator 4 is applied to the X input of four quadrant multiplier 6. It is important for purposes of this circuit that multiplier 6 be a four quadrant multiplier so that it may deal with both positive and negative signals. The output of operational amplifier 2 is also applied to the Y input of multiplier 6. At multiplier 6, the Y input is multiplied by the X input so that a product output signal from multiplier 6 is obtained which is in phase with the output of operational amplifier 2. The output of multiplier 6 is applied to the positive input of operational amplifier 2. In this manner, the voltage fed back to the X input of multiplier 6 is automatically adjusted so that the value of the signal at the Y input of multiplier 6 is amplified appropriately to cause resonant feedback when fed to the positive input of operational amplifier 2. Thus, the detector maintains a constant amplitude of oscillation, even as the resonant frequency shifts.

The output signal from integrating comparator 4 is not only fed back to multiplier 6 but is applied through gain and offset amplifier 7 to an A/D input of microprocessor 8. This voltage reflects the resistance of the series resonant circuit which changes with temperature, namely the variable resistance of the inductor. Microprocessor 8 has stored within it or in its associated ROM 9 the period of the resonant frequency of the oscillator when no debris particles are present on the inductor in series resonance network 1. In use, as the inductance changes, the period of oscillation will change. The program within microprocessor 8 measures the change in the period between the presently measured period and the stored initial period. The change in period is the measure of the change in inductance of the inductor which in turn is a measure of the number of debris particles which have been drawn by the magnet to the inductor probe. Simultaneously, the microprocessor 8 is provided at an A/D input, the signal which is proportional to the temperature variation of the probe. Using an appropriate algorithm microprocessor 8 applies a correction or compensation to the measured period as correction for the nonlinear temperature effects on the inductor. As mentioned above, the system may be interrogated through a standard RS-232 serial interface 10 for various types of information including the current resonant period, the temperature correction applied, or the temperature corrected period information.

Figure 4A:
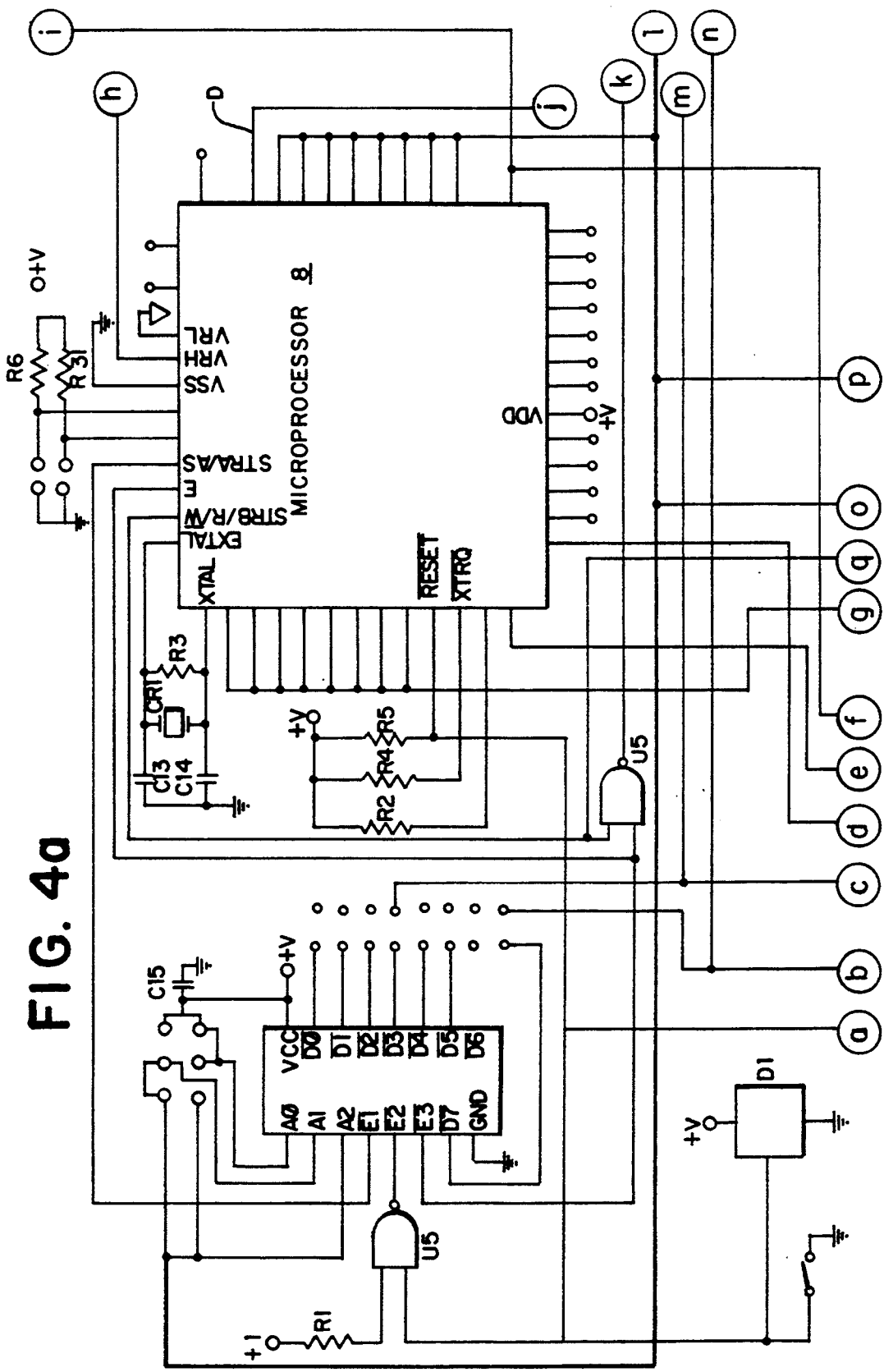
FIGS. 4A, 4B, and 4C detailed schematic diagrams of the sensor, oscillator, and microprocessor circuitry.
Figure 4B:
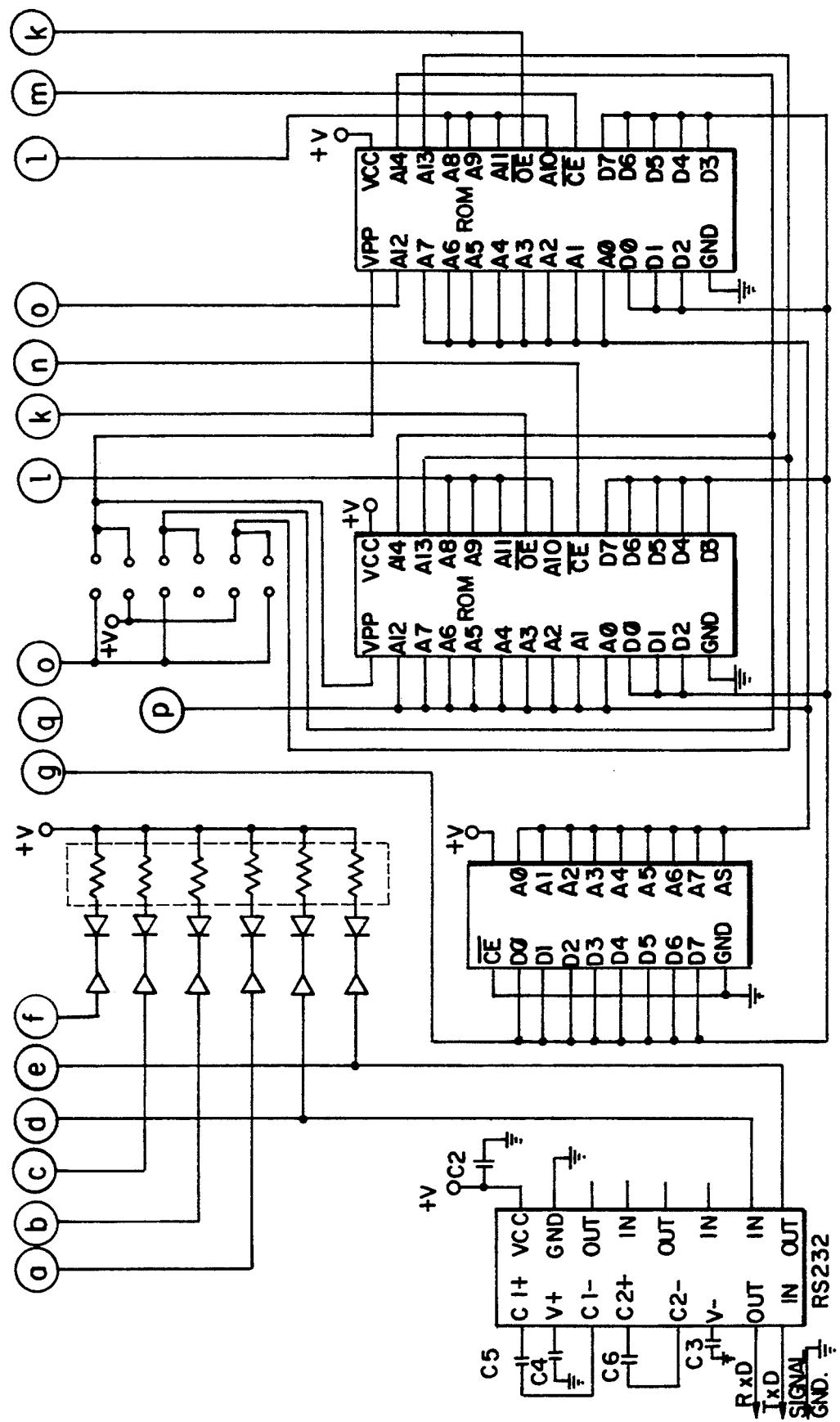
Figure 4C:
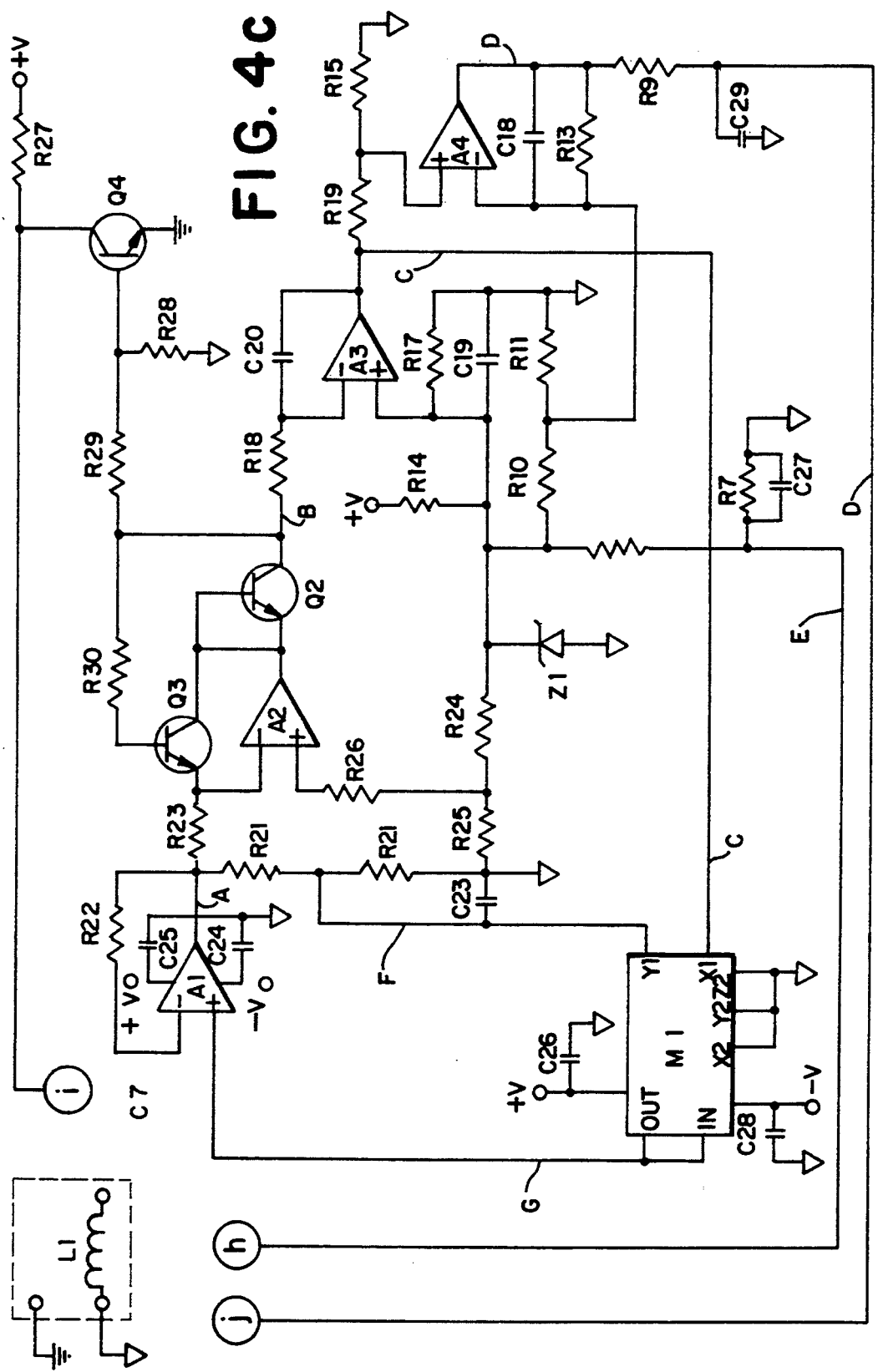

FIGS. 4A, 4B, and 4C are a full schematic diagram of the detector of the system of this invention.

Coil L1 is the inductor as it would be present in probe 68. Coil L1 in conjunction with capacitor C17 makes up the series resonance network. The series resonance network is connected to the negative input of amplifier A1. The output A of amplifier A1 is applied to the rectifier circuitry consisting of amplifier A2 and transistors Q2, Q3 and Q4. The rectified signal appearing at the collector of Q4 is applied to the period measurement (input capture) line 8 of microprocessor 8. The rectified output at B is applied to integrator comparator amplifier A3 with input resister R18 and feedback capacitor C20. The output of the integrator comparator is applied on line C to the X input of multiplier M1. The output of the integrator comparator is also applied through voltage divider network RL19 and R15 to the positive input of gain and offset amplifier A4. The output of gain and offset amplifier A4 on line D is applied to the A/D input on line 17 of the microprocessor 8. A reference voltage is also derived on line E which is applied to VRH input line 22 of microprocessor 8. The output A of amplifier A1 is also applied through voltage divider network 20 and 21 on line F to the Y input of multiplier M1. Multiplier M1 is a four quadrant multiplier that has as its output the product of X times Y. The signal appearing on F is therefore multiplied by the value of the signal coming in to multiplier M1 on line C. The output of multiplier M1 on line G is applied to the positive input of amplifier A1 and completes the feedback loop.

Microprocessor 8 has an external crystal oscillator input at lines 29 and 30 which provides a regulated time base to microprocessor 8. The microprocessor program counts the number of pulses arriving at input line 8 per period of time and calculates thereby a period of oscillation of the resonant circuit. Microprocessor 8 has both internally, and connected to it on the address bus, ROM memory in which can be stored the value of the oscillator period associated with inductor L1 when L1 has no debris particles attached. As debris particles accumulate, the inductance of L1 changes, thereby changing the period of oscillation of the series resonant oscillator. The microprocessor 8 measures the new period and calculates the difference between the new period and the stored reference period. The change in the period is a measure of the inductance change in inductor L1 and therefore of the amount of debris particles which have accumulated. Since the inductor L1 is subject to extreme temperature changes, the inductance will change with temperature. The resistance through the inductor as noted above will also change with temperature. The output signal from the gain and offset amplifier on line D is converted by the A/D input of microprocessor 8 into a digital value which can be used in connection with an algorithm built into the software of microprocessor 8 to correct the change in period observed in the oscillator for the effect of change in temperature. Thus, microprocessor 8, by correcting the change in period, or the measured value of the inductance, for temperature provides an accuracy of inductance measurement heretofore not available in the prior art. For example, the total change in oscillator frequency typically seen in resonance circuits of this nature, where the inductance has been changed by accumulation of debris particles, is on the order of approximately two percent. At the same time, the change of inductance due to temperature effects may be on the order of one percent. Therefore, it can quite clearly be seen that, unless the effects of temperature are carefully controlled for, the signal of interest can be vastly distorted by the consequence of the change in the temperature on the inductor. The circuitry of the present system improves, by at least a factor of four, the accuracy of the correction for temperature that can be achieved with the inductor L1.

That is, the accuracy is approximately four times better when a probe incorporating inductor L1 is used in the series resonant circuit of the present invention as opposed to using the same inductor probe in a parallel resonant circuit of the prior art.

The schematic of FIG. 4 provides for additional ROM memory storage which can be selected by appropriate addressing. In addition, a standard RS-232 serial output is provided. Through the RS-232 output, microprocessor 8 can be interrogated. Various types of information are available from the microprocessor. For instance, the current frequency of the resonant oscillator is available, the change in frequency at the present moment compared to the initial conditions is available, and the value and degree of the temperature correction being applied is available. This data may be stored by the microprocessor for predetermined amounts of time pending interrogation. It is known that debris particles of larger size are frequently generated in mechanical systems immediately before failure of those systems. It is also known that a more rapid increase in the concentration of debris particles is seen immediately before failure of the mechanical parts. Therefore, it is possible to have the program in the microprocessor identify and set aside into separate memory incidents of major changes in inductance which would be reflective of either larger particles or a more rapid particle buildup over a given period of time. The microprocessor may similarly be interrogated with respect to the occurrence of these type of changes in the system.

Thus, it can be seen that the system of the present invention provides a means to precisely measure changes in inductance of a coil, even when the coil is undergoing extreme temperature changes. In the present invention, an example is given in the use of a particle chip detector, but the circuit is equally applicable to other systems where the sensor is composed of a variable inductance.

What is claimed is:

1. A means for sensing ferrous particles entrained in a fluid comprising:
    (a) a magnet having two poles, a first one of which is positioned within said fluid;
    (b) a coil formed from an electrically-conductive material located coaxially with a second pole of said magnet;
    (c) a series resonant electronic circuit for measuring the inductance of said coil, said circuit being connected to said coil, said series resonant circuit comprising:
        1. a series resonant network of said coil;
        2. a capacitor;
        3. a series resonant oscillator comprising an amplifier having a series resonant network connected to its inverting input, a rectifier, an integrator comparator, and a multiplier, wherein the output of said amplifier is applied to a first input of said multiplier before being rectified and applied to the input of the integrator comparator, the output of the integrator comparator being applied to a second input of said multiplier, the output of the multiplier being applied to the non-inverting input of said amplifier;
        4. a gain and offset amplifier; and
        5. a microprocessor for determining a temperature compensation in response to the period of oscillation and a single representative of the gain of said amplifier;
    wherein the output of said microprocessor is a signal representative of the temperature compensated inductance of said coil, and thus is also representative of the amount of ferrous material accumulated on or immediately adjacent to said first pole of said magnet.

2. A means for sensing ferrous particles entrained in a fluid comprising:
    (a) a magnet having two poles, a first one of which is positioned within said fluid;
    (b) a coil formed from an electrically-conductive material located coaxially with a second pole of said magnet;
    (c) a series resonant electronic circuit for measuring the inductance of said coil, said circuit being connected to said coil; said series resonant circuit comprising:
        1. a series resonant network of said coil;
        2. a capacitor;
        3. a series resonant oscillator;
        4. a gain and offset amplifier; and
        5. a microprocessor for determining a temperature compensation in response to the period of oscillation and a single representative of the gain of said amplifier;
    wherein a first input to said microprocessor is connected to the output from said rectifier, and wherein said microprocessor captures the output from said rectifier, and further wherein a second input to said microprocessor is connected through an analog to digital converter to a signal representative of the state of said gain and offset amplifier which is proportional to the voltage across said series resonance network.

* * * * *